United States Patent [19]

Tanigawa

[11] Patent Number: 5,516,735
[45] Date of Patent: *May 14, 1996

[54] METHOD FOR STABILIZING RHODIUM COMPOUND

[75] Inventor: Hiroto Tanigawa, Hyogo, Japan

[73] Assignee: Daicel Chemical Industries, Ltd., Osaka, Japan

[*] Notice: The term of this patent shall not extend beyond the expiration date of Pat. No. 5,385,875.

[21] Appl. No.: 327,330

[22] Filed: Oct. 21, 1994

Related U.S. Application Data

[63] Continuation of Ser. No. 184,981, Jan. 24, 1994, Pat. No. 5,385,875.

[30] Foreign Application Priority Data

Mar. 31, 1993 [JP] Japan ................................ 5-073375

[51] Int. Cl.$^6$ ................................................ B01J 20/34
[52] U.S. Cl. ......................... 502/24; 502/30; 502/32; 562/895; 562/898
[58] Field of Search .......................... 502/24, 30, 32; 562/895, 898

[56] References Cited

U.S. PATENT DOCUMENTS

| | | | |
|---|---|---|---|
| 4,476,238 | 10/1984 | Palmer et al. | 502/31 |
| 4,735,749 | 4/1988 | Fujiwa et al. | 502/33 |
| 5,385,875 | 1/1995 | Tanigawa | 502/24 |

Primary Examiner—Asok Pal
Attorney, Agent, or Firm—Flynn, Thiel, Boutell & Tanis

[57] ABSTRACT

A concentrated catalyst solution provided in the carbonylation reaction in which methyl acetate or dimethyl ether is chemically bonded with carbon monoxide in the presence of a catalyst system comprising a rhodium compound and an alkali metal iodide to produce acetic anhydride is subjected to a carbonylation treatment with carbon monoxide or a mixture of carbon monoxide and hydrogen before it is applied to a process for separating the tar contained in the catalyst solution, thereby increasing the iodide ion content of the catalyst solution, thus enabling the rhodium compound to be stabilized.

When the concentration of the iodide ion in the concentrated catalyst solution is increased by this method, there is no possibility of the balances between the rhodium concentration and, the alkali metal concentration and the iodine concentration of the carbonylation reaction system being disturbed even when the catalyst solution as reprocessed is returned to the carbonylation reaction system. Further, the increase in the iodide ion concentration of the concentrated catalyst solution enables the rhodium compound contained in the concentrated catalyst solution to be stabilized, which prevents the rhodium compound from settling from the catalyst solution even during the heat treatment conducted for the purpose of removing components each having a low-boiling point contained in the catalyst solution before the process for separating and removing tar from the concentrated catalyst solution, so that the loss of the very expensive rhodium compound can be minimized.

24 Claims, No Drawings

METHOD FOR STABILIZING RHODIUM COMPOUND

This is a continuation of Ser. No. 08/184,981, filed Jan. 24, 1994, now U.S. Pat. No. 5,385,875.

BACKGROUND OF THE INVENTION

1. Field of the Invention

The present invention relates to a method for stabilizing a rhodium compound and more particularly to a method for stabilizing a rhodium compound contained in a catalyst solution contaminated with tar formed as a by-product in the carbonylation reaction in which methyl acetate or dimethyl ether is chemically bonded with carbon monoxide in the presence of a catalyst system comprising a rhodium compound and an alkali metal iodide to produce acetic anhydride.

2. Description of the Related Art

A reaction of carbon monoxide, alone or together with hydrogen, with methyl acetate or dimethyl ether in the presence of a rhodium catalyst to produce acetic anhydride is very useful from the viewpoint of industry. It is known that the addition of various cocatalysts is useful for this reaction It is also well known that the most serious problem of this reaction resides in a lowering in the reactivity due to accumulation of tar as a by-product. For this reason, in order to conduct this reaction on an industrial scale, it is necessary to remove the tar outside the system.

In the above-described reaction, since use is generally made of a homogeneous catalyst, the tar and rhodium catalyst are contained in one and the same solution. Therefore, the development of an efficient tar/rhodium separation process capable of minimizing the loss of the rhodium compound, which is a very expensive catalyst, is indispensable to the practice of the above-described reaction on an industrial scale.

Typical examples of the tar/rhodium separation processes of the type described above include (1) extraction with an aqueous methyl iodide/hydroiodic acid solution, (2) precipitation/insolubilization of a rhodium complex by heat treatment and (3) extraction with an alkane or a cycloalkane (see U.S. Pat. No. 4,476,238; published on Oct. 9, 1984; Halcon-SD-Group Inc.). Among these processes, the process (1) has a drawback that, since the reaction system is contaminated with hydroiodic acid, a compound containing iodine should be removed outside the reaction system for the purpose of keeping the balance between the rhodium concentration and the iodine concentration in the reaction system. The process (2) has a drawback that this process is very complicate due to the occurrence of sedimentation of the rhodium compound as a solid. The process (3) has none of the above-described problems and enables the tar/rhodium separation to be conducted in a very simple manner (see the above described U.S. Pat. No. 4,476,238).

However, as described also in the U.S. Pat. No. 4,476,238, in the process (3), accumulation of various compounds in the extractant should be prevented. Specifically, the extractant after the extraction and the compound contained therein should be substantially separated from each other by an industrially practicable operation such as distillation. Since, however, alkanes and cycloalkanes, for example, pentane and cyclohexane, generally form azeotropes with components each having a low-boiling point contained in large amounts in the reaction system for the above-described acetic anhydride formation, such as methyl iodide and methyl acetate, not only it is difficult to separate these compounds from the extractant by distillation but also other separation operations are also difficult to conduct on an industrial scale. For this reason, before the catalyst solution to be extracted, which is generally a concentrated catalyst solution provided by flash vaporization of a carbonylation reaction mixture (hereinafter referred to simply as "concentrated catalyst solution"), is applied to a tar extraction process using an alkane and a cycloalkane, components each having a low-boiling point contained in the catalyst solution, such as methyl iodide and methyl acetate, should be separated by distillation.

However, studies conducted by the present inventors have revealed that some rhodium complexes contained in the concentrated catalyst solution are highly liable to sediment upon being heat-treated at a temperature of around the boiling point of the concentrated catalyst solution. The reason for this will now be described.

The rhodium catalyst contained in the concentrated catalyst solution has been found to comprise a mixture of the following four complexes by IR spectroscopy:

(a) $[Rh^+(CO)_2I_2]^-$ (2060, 1990 cm$^{-1}$), (b) $[Rh^{3+}(CO)_2I_4]^-$ (2085 cm$^{-1}$), (c) $[Rh^{3+}(CO)I_4]^-$ (2064 cm$^{-1}$), and (d) $[Rh^{3+}(CO)I_5]^{2-}$ (2035 cm$^{-1}$).

It can be easily perceived that, among these complexes, the rhodium complex (c) having an unsaturated coordination is thermally unstable. In fact, as is apparent from Reference Example 1 which will be described later, studies conducted by the present inventors have revealed that the concentrated catalyst solution containing the rhodium complex (c) is more unstable in the heat treatment than the concentrated catalyst solution not containing the rhodium complex (c). Here, it is to be noted that the rhodium complex (c) is thought to be converted into a rhodium complex (d) when it is reacted with an iodide ion.

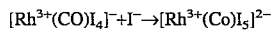

Therefore, it is expected that, if the concentration of the iodide ion in the concentrated catalyst solution is sufficiently high, the concentrated catalyst solution is substantially free from the rhodium complex (c), so that the concentrated catalyst solution would be stable in the heat treatment. In fact, as is apparent from Reference Example 2 which will be described later, studies conducted by the present inventors have revealed that, when the molar ratio of the iodide ion to rhodium [hereinafter referred to as "I/Rh (molar ratio)"] is 20 or more, the rhodium complex (c) is absent in the concentrated catalyst solution, so that the concentrated catalyst solution is stable also in the heat treatment at the boiling point of the concentrated catalyst solution. Therefore, it is conceivable that, if the reaction for producing acetic anhydride is conducted in the presence of a catalyst system having such a composition that an alkali metal iodide exists in an amount of 20 mol or more per mol of a rhodium compound, the I/Rh (molar ratio) becomes 20 or more, so that the concentrated catalyst solution would be stable in the heat treatment. This method, however, has a serious problem.

The problem is that under the carbonylation reaction conditions, the alkali metal iodide is reacted with methyl acetate within the reactor, which causes most of the alkali metal iodide to be converted into an alkali metal salt of acetic acid, such as lithium acetate, and methyl iodide unfavorably. In this connection, the present inventors have found that, as is apparent from Reference Example 3 which will be described later, when the reaction has reached a steady state, the iodide ion concentration is apparently lower than that in a stage of initial charging. For this reason, in order to maintain the I/Rh (molar ratio) in the concentrated catalyst solution at 20 or more, it is necessary to add the iodide in considerable excess over the necessary amount. This is disadvantageous from the viewpoints of an increase in the amount of tar formed as a by-product and an increase in the cost. Therefore, it is substantially impossible to successfully conduct the tar/rhodium separation by extraction with an alkane or a cycloalkane on an industrial scale unless the abovedescribed problem is solved.

The addition of an alkali metal iodide or hydroiodic acid to the concentrated catalyst solution to increase the iodide ion concentration is deemed effective as one method for solving the problem. In this method, however, an alkali metal and/or iodine are added to the concentrated catalyst solution from the outside of a series of reaction systems. For this reason, in order that the concentrated catalyst solution containing the alkali metal and/or iodine added may be reprocessed and used as the catalyst for the carbonylation reaction in which methyl acetate or dimethyl ether is chemically bonded with carbon monoxide to form acetic anhydride, balances between the rhodium concentration and, the alkali metal concentration and the iodine concentration in the carbonylation reaction system should be kept, so that the compounds containing these elements should be withdrawn in an amount corresponding to the amount of added elements from the concentrated catalyst solution or the catalyst solution after the catalyst reprocessing treatment. Since, however, the compounds containing alkali metals exist in the form of salts completely soluble in the (concentrated) catalyst solution, it is difficult to selectively remove these compounds by the conventional techniques. On the other hand, the iodine-containing compound exists as methyl iodide and, therefore, can be separated by distillation. However, the separated methyl iodide is a highly toxic compound, which renders the treatment thereof very difficult.

DISCLOSURE OF THE INVENTION

SUMMARY OF THE INVENTION

An object of the present invention is to provide a method for stabilizing a rhodium compound through an increase in the iodide ion concentration of a concentrated catalyst solution or a method for regenerating a catalyst, which method enables the balances between the rhodium concentration and, the alkali metal concentration and the iodine concentration in the carbonylation reaction system, in which methyl acetate or dimethyl ether is chemically bonded with carbon monoxide to produce acetic anhydride, to be kept unchanged even when the reprocessed catalyst solution is returned without the removal of an alkali metal and/or iodine from the (concentrated) catalyst solution to the carbonylation reaction system.

The present inventors have made extensive studies with a view to solving the above-described problems and, as a result, have found that the iodide ion concentration of the concentrated catalyst solution can be increased to stabilize the rhodium compound by subjecting the concentrated catalyst solution to a treatment (carbonylation treatment) with carbon monoxide or a mixture of carbon monoxide and hydrogen to produce a metal iodide from methyl iodide and methyl acetate contained in the concentrated catalyst solution, which has led to the completion of the present invention.

Thus, the present invention provides a method for stabilizing a rhodium compound contained in a catalyst solution contaminated with tar formed as a by-product in the carbonylation reaction in which methyl acetate or dimethyl ether is chemically bonded with carbon monoxide in the presence of a catalyst system comprising a rhodium compound and an alkali metal iodide to produce acetic anhydride, wherein the catalyst solution as such or alternatively a catalyst solution mixture formed by adding a diluent comprising at least one of the compounds present in the carbonylation reaction system to the catalyst solution is treated with carbon monoxide or a mixture of carbon monoxide and hydrogen before the catalyst solution or the catalyst solution mixture is applied to a process for separating the tar contained in the catalyst solution.

Further, the present invention provides a method for regenerating a catalyst solution contaminated with tar formed as a by-product in the carbonylation reaction in which methyl acetate or dimethyl ether is chemically bonded with carbon monoxide in the presence of a catalyst system comprising a rhodium compound and an alkali metal iodide to produce acetic anhydride, which comprises the step that the catalyst solution as such or alternatively a catalyst solution mixture formed by adding a diluent comprising at least one of the compounds present in the carbonylation reaction system to the catalyst solution is treated with carbon monoxide or a mixture of carbon monoxide and hydrogen before the catalyst solution or the catalyst solution mixture is applied to a process for separating the tar contained in the catalyst solution.

Further scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention will now be described in detail.

The synthesis of acetic anhydride by carbonylating methyl acetate in the presence of a catalyst system containing a rhodium compound and an alkali metal iodide can be represented by the following reaction scheme. Although the counter cation of the iodide ion may be any of alkali metal cations, metallic cations other than the alkali metal cations and organic cations, the present invention will now be described with reference to lithium ion as a representative counter cation of the iodide. When dimethyl ether is used as the starting compound instead of methyl acetate, dimethyl ether is reacted with carbon monoxide to form methyl acetate from which acetic anhydride is similarly synthesized according to the following reaction scheme:

$$CH_3COOCH_3 + LiI \rightarrow CH_3COOLi + CH_3I \qquad (1)$$

$$CH_3I + CO \rightarrow CH_3COI \qquad (2)$$

$$CH_3COI + CH_3COOLi \rightarrow CH_3COOCOCH_3 + LiI \qquad (3)$$

According to the above-described reaction formulae (1) to (3), when the supply of methyl acetate is sufficient, lithium iodide formed by the reaction represented by the formula (3)

is again reacted with methyl acetate according to the reaction formula (1) and thereby converted into methyl iodide. On the other hand, when a solution containing methyl iodide and lithium acetate or a solution containing methyl iodide, lithium acetate and methyl acetate is subjected to a carbonylation treatment without the supply of methyl acetate, the reaction represented by the formula (1) is suspended when the methyl acetate has completely been consumed, so that only the reactions represented by the formulae (2) and (3) proceed. This results in the formation of lithium iodide from lithium acetate and methyl iodide, so that the iodide ion concentration of the reaction system is increased and so is the I/Rh (molar ratio). In fact, studies conducted by the present inventors have revealed that when a concentrated catalyst solution containing at least a rhodium catalyst, methyl iodide, methyl acetate and lithium acetate and provided by the carbonylation reaction of methyl acetate is subjected to a carbonylation treatment by externally adding carbon monoxide or carbon monoxide and hydrogen, the iodide ion concentration of the concentrated catalyst solution is increased about twice to four times that before the treatment. The present invention has been made based on this fact.

The catalyst solution to be treated by the above-described method is generally a solution containing a catalyst (a concentrated catalyst solution) provided by removing acetic anhydride by flash vaporization or other method from a reaction mixture produced by a process wherein acetic anhydride is produced by carbonylating methyl acetate or dimethyl ether under the following conditions.

In the catalyst used in the carbonylation reaction, examples of the rhodium compound include inorganic rhodium salts, such as rhodium chloride, rhodium bromide, rhodium iodide and rhodium nitrate, rhodium carboxylates, such as rhodium acetate, organic rhodium complexes, such as rhodium acetylacetonate, rhodium/amine complex salts, trichlorotrispiridinerhodium and carbonylhydridotris(triphenylphosphine)rhodium, and cluster complexes, such as dodecacarbonyl tetrarhodium. Among them, rhodium iodide is particularly preferred.

Although, there is no strict limitation on the amount of the rhodium compound used, the rhodium compound is used in an amount in the range of from 0.1 to 50 mmol/l, preferably in the range of from 10 to 30 mmol/l, in terms of the rhodium compound concentration in the reaction solution.

Examples of the alkali metal iodide constituting the catalyst system include lithium iodide, sodium iodide and potassium iodide. Lithium iodide is particularly preferred.

In addition to the rhodium compound and alkali metal iodide, aluminum compounds and boron compounds may be used as the cocatalysts.

Examples of the aluminum compound include carboxylates of aluminum, such as aluminum formate, aluminum acetate and aluminum propionate, aluminum alkoxides, such as methoxyaluminum, ethoxyaluminum and isopropoxyaluminum, halides of aluminum, such as aluminum chloride, aluminum bromide and aluminum iodide, and metallic aluminum.

Examples of the boron compound include boric acid, metaboric acid, borohydric acid, lithium borohydride, sodium borohydride, boron acetate and esters of boric acid.

In the process for producing acetic anhydride by the carbonylation of methyl acetate or dimethyl ether, that is, carbonylation reaction, the reaction temperature is usually in the range of from 130° to 250° C., preferably in the range of from 150° to 200° C. The partial pressure of carbon monoxide within the reactor during the reaction is in the range of from 1 to 100 atm, preferably in the range of from 10 to 50 atm, while the partial pressure of hydrogen is in the range of from 0.1 to 5 atm, preferably in the range of from 0.1 to 2 atm.

Flash vaporization is usually conducted for the purpose of obtaining acetic anhydride as a product from the reaction mixture after the completion of the carbonylation reaction, and the reaction mixture is divided into a distillate containing acetic anhydride and a concentrated catalyst solution containing catalyst components. In the present invention, this concentrated catalyst solution is subjected to a carbonylation treatment with carbon monoxide or a mixture of carbon monoxide and hydrogen. There is no particular limitation on the flash vaporization ratio in the flash vaporization which is a step prior to the carbonylation treatment. The flash vaporization is usually conducted with the flash vaporization ratio of from 10 to 90%, preferably from 30 to 60%.

In the present invention, the concentrated catalyst solution containing catalyst components thus provided is subjected to a carbonylation treatment with carbon monoxide or a mixture of carbon monoxide and hydrogen before it is subjected to the tar separation step. In the carbonylation treatment, the reaction conditions may be the same as those used in the acetic anhydride production process. Further, it is a matter of course that there is no need to externally add fresh catalyst components from the outside because the concentrated catalyst solution contains all the catalyst components necessary for the carbonylation treatment.

Although there is no particular limitation on the composition of the concentrated catalyst solution to be subjected a carbonylation treatment, it is preferred that the methyl iodide concentration be 5 to 50% by weight, preferably 10 to 30% by weight, from the viewpoint of the reaction rate. In order to meet this requirement, the carbonylation treatment is preferably conducted after methyl iodide as such or a solution containing methyl iodide is added to the concentrated catalyst solution. In order to keep the iodine balance, i.e., the balance between iodine and rhodium, in the carbonylation reaction system in which methyl acetate or dimethyl ether is chemically bonded with carbon monoxide to produce acetic anhydride and to which the catalyst solution after the regeneration treatments including a carbonylation treatment is added, it is particularly preferred to use, as the solution containing methyl iodide to be added before the carbonylation treatment, a part of the circulating stream within a series of steps (comprising the step of conducting the carbonylation reaction and the step of regenerating the catalyst).

The carbonylation treatment may be applied to a concentrated catalyst solution which has been diluted with a diluent comprising at least one compound present in the carbonylation reaction systems represented by the formulae (1) to (3), for example, acetic anhydride, for the purpose of preventing the precipitation of the catalyst components during distillation or extraction conducted before or after the carbonylation treatment.

The present invention provides a method for increasing the iodide ion concentration of the concentrated catalyst solution, which method does not disturb the balances between the rhodium concentration and, the alkali metal concentration and the iodine concentration in the carbonylation reaction system in which methyl acetate or dimethyl ether is chemically bonded with carbon monoxide to produce acetic anhydride, even when the (concentrated) catalyst solution as reprocessed is returned without the removal of an alkali metal and/or iodine from the (concentrated) catalyst solution to the carbonylation reaction system. The increase in the iodide ion concentration by this method enables the rhodium compound contained in the concentrated catalyst solution to be stabilized, which prevents the rhodium compound from settling from the catalyst solution even during the heat treatment conducted for the purpose of removing components each having a low-boiling point contained in the catalyst solution before the steps of separating and removing tar from the concentrated catalyst solution, so that the loss of the very expensive rhodium compound can be minimized.

EXAMPLES

The present invention will now be described in more detail with reference to the following Examples.

Regarding the analysis of various components described in the following Examples, gas chromatography was used for the liquid components, ICP emission spectroscopic analysis for the metallic components and titration using silver nitrate for the iodide ion. In the Examples, although the method according to the present invention is described by referring to a batch reaction, it is needless to say that the method according to the present invention can be conducted by a continuous reaction.

Reference Example 1 (Influence of structure of rhodium complex on heat stability)

A concentrated catalyst solution containing rhodium complexes, all of which belonged to the above-described rhodium complex (b), was heated at 120° C. for one hr. As a result of the analysis of metals for the concentrated catalyst solution before and after the heat treatment, it was found that no sedimentation of rhodium occurred.

Separately, a concentrated catalyst solution containing, as the rhodium complex, 60% of the rhodium complex (b) and 40% of the rhodium complex (c) was heated at 120° C. for one hr. As a result of the analysis of metals for the concentrated catalyst solution before and after the heat treatment, it was found that 31% of rhodium was sedimented.

Reference Example 2 (Influence of iodine ion content on rhodium complex structure)

Solutions prepared by adding 5.0 g of rhodium iodide and lithium iodide in amounts to provide I/Rh (molar ratio) values of 10, 20 and 30 to 130 g of acetic anhydride were put in an autoclave having an internal volume of 300 ml, and carbon monoxide and hydrogen were fed into the autoclave in respective partial pressures of 15 kg/cm$^2$G and 15 kg/cm$^2$G to cause a reaction among them at 190° C. for 3 hr. 70 g of each homogeneous solution after complete dissolution of the solid matter was put in a glass flask, where it was heat-treated at 125° C. for one hr in a nitrogen atmosphere. After the completion of cooling, the structures of the rhodium complexes contained in the contents of the autoclave were analyzed by IR spectroscopy. The results were as given in Table 1.

TABLE 1

| I/Rh (molar ratio) | Rhodium complex (b) | Rhodium complex (c) | Rhodium complex (d) |
| --- | --- | --- | --- |
| 10 | 80% | 20% | 0% |
| 20 | 80% | 0% | 20% |
| 30 | 60% | 0% | 40% |

As is apparent from Table 1, when a solution having an I/Rh (molar ratio) of 10 was subjected to the reaction and heat treatment, the formation of the rhodium complex (c) in a minor amount was observed, whereas when a solution having an I/Rh (molar ratio) of 20 or 30 was subjected to the reaction and heat treatment, no formation of the rhodium complex (c) was observed at all.

The solutions as heat-treated were then centrifuged. As a result, a black sediment occurred from the reaction mixture provided by subjecting the solution having an I/Rh (molar ratio) of 10 to the reaction and heat treatment, whereas no sediment occurred from the reaction mixture provided by subjecting the solution having an I/Rh (molar ratio) of 20 or 30 to the reaction and heat treatment.

Reference Example 3 (Reduction in iodide ion concentration due to reaction of lithium iodide with methyl acetate)

Methyl acetate and methanol were carbonylated in a small-size continuous reaction device provided with a pressure reactor having an internal volume of 500 ml under conditions of 190° C. and 28 kg/cm$^2$G to produce acetic anhydride and acetic acid in respective amounts of 350 g/hr and 290 g/hr. The reaction mixture in a steady state contained methyl iodide, methyl acetate, acetic acid and acetic anhydride in respective amounts of 18%, 24%, 24% and 31% and, as a catalyst system, 0.6% of rhodium and lithium, aluminum and boron in respective amounts of 20 times, 5 times and 23 times, by mole, that of rhodium.

The iodide ion content of the reaction mixture immediately after the initiation of the reaction was 23 times, by mole, that of rhodium, whereas after the steady state had reached, the iodide ion content of the reaction mixture was as low as 4 times, by mole, that of rhodium.

Example 1 (Carbonylation treatment of concentrated catalyst solution)

160 of a concentrated catalyst solution, which had been provided by a carbonylation reaction and subsequent flash vaporization and contained 3.3% of methyl iodide, 16.5% of methyl acetate, 34.9% of acetic anhydride, 38.5% of acetic acid, 0.12% of rhodium, 0.16% of aluminum, 0.19% of boron, 0.13% of lithium and 0.55% of iodide ion, was put in an autoclave having an internal volume of 500 ml, and carbon monoxide and hydrogen were fed into the autoclave in respective partial pressures of 40 kg/cm$^2$G and 4 kg/cm$^2$G to cause a reaction among them, i.e., to conduct a carbonylation treatment, at 190° C. for 3 hrs. After the reaction mixture, i.e., the treated concentrated catalyst solution, was cooled and subjected to pressure relief, the iodide ion concentration was determined and found to be 1.2% that was about 2.2 times that of the concentrated catalyst solution before the carbonylation treatment.

Example 2 (Heat treatment of solution after carbonylation treatment)

90 g of the solution as carbonylated (i.e., treated with carbon monoxide and hydrogen) provided in Example 1 was put in a glass flask having an internal volume of 100 ml, and components each having a low-boiling point were removed by distillation under atmospheric pressure until the weight of the contents of the glass flask reached 40 g. The time taken to remove the components each having a low-boiling point by the distillation was 50 min, and the solution temperatures at the initiation of the distillation and at the end of the distillation were 50° C. and 132° C., respectively. The content of the glass flask was cooled and then centrifuged. As a result, no sedimentation was observed. The result of the analysis of metals for the solution after the distillation, i.e., the amount of the rhodium contained in the solution after the distillation, was in agreement with that of the analysis of metals for the solution before the distillation, i.e., the amount of the rhodium contained in the solution before the distillation, with an error within an acceptable limit.

Example 3 (Carbonylation treatment-1 of concentrated catalyst solution supplemented with methyl iodide)

160 g of a catalyst solution, which had been provided by adding methyl iodide to a concentrated catalyst solution after a carbonylation reaction and subsequent flash vaporization and contained 21.7% of methyl iodide, 13.2% of methyl acetate, 26.5% of acetic anhydride, 31.2% of acetic acid, 0.09% of rhodium, 0.13% of aluminum, 0.15% of boron, 0.11% of lithium and 0.46% of iodide ion, was put in an autoclave having an internal volume of 500 ml and carbonylated (i.e., treated with carbon monoxide and hydrogen) in the same manner as that of Example 1. The iodide ion concentration of the catalyst solution as treated was determined and found to be 1.8% which was about 3.9 times the concentration of the catalyst solution before the carbonylation treatment.

The catalyst solution after the completion of the carbonylation treatment was heat-treated in the same manner as that of Example 2. As a result, no sedimentation of the rhodium compound was observed.

Example 4 (Carbonylation treatment-2 of concentrated catalyst solution supplemented with methyl iodide)

160 g of a catalyst solution, which had been provided by adding methyl iodide to a concentrated catalyst solution after a carbonylation reaction and subsequent flash vaporization and contained 23.1% of methyl iodide, 9.5% of methyl acetate, 16.3% of acetic anhydride, 38.0% of acetic acid, 0.09% of rhodium, 0.14% of aluminum, 0.17% of boron, 0.42% of sodium and 1.45% of iodide ion, was put in an autoclave having an internal volume of 500 ml and carbonylated (i.e., treated with carbon monoxide and hydrogen) in the same manner as that of Example 1. The iodide ion concentration of the catalyst solution as treated was determined and found to be 2.4% which was about 1.7 times the concentration of the catalyst solution before the carbonylation treatment.

The catalyst solution after the completion of the carbonylation treatment was heat-treated in the same manner as that of Example 2. As a result, no sedimentation of the rhodium compound was observed.

Example 5 (Carbonylation of concentrated catalyst solution supplemented with methyl iodide and acetic anhydride)

160 g of a catalyst solution, which had been provided by adding methyl iodide and acetic anhydride to a concentrated catalyst solution after a carbonylation reaction and subsequent flash vaporization and contained 20.8% of methyl iodide, 6.0% of methyl acetate, 38.5% of acetic anhydride, 26.7% of acetic acid, 0.06% of rhodium, 0.10% of aluminum, 0.13% of boron, 0.34% of sodium and 0.95% of iodide ion, was put in an autoclave having an internal volume of 500 ml and carbonylated (i.e., treated with carbon monoxide and hydrogen) in the same manner as that of Example 1. The iodide ion concentration of the catalyst solution as treated was determined and found to be 2.05% which was about 2.2 times the concentration of the catalyst solution before the carbonylation treatment.

The catalyst solution after the completion of the carbonylation treatment was heat-treated in the same manner as that of Example 2. As a result, no sedimentation of the rhodium compound was observed.

Comparative Example 1

90 g of the same concentrated catalyst solution as that used for subjecting the carbonylation treatment, i.e., the concentrated catalyst solution not to be subjected the carbonylation treatment, in Example 1 was heat-treated (distilled) in the same manner as that of Example 2. After the content was cooled, it was centrifuged. As a result, sedimentation of a black solid was observed. The analyses of metals for the solutions before and after the distillation revealed that 35%, based on the amount of the rhodium contained in the solution before distillation, of rhodium was sedimented during distillation, etc.

Comparative Example 2

90 g of the same concentrated catalyst solution as that used for subjecting the carbonylation treatment in Example 3 was heat-treated (distilled) in the same manner as that of Example 2. After the content was cooled, it was centrifuged. As a result, sedimentation of a black solid was observed. The analyses of metals for the solutions before and after the distillation revealed that 30%, based on the amount of the rhodium contained in the solution before distillation, of rhodium was sedimented during distillation, etc.

Comparative Example 8

90 g of the same concentrated catalyst solution as that used for subjecting the carbonylation treatment in Example 4 was heat-treated (distilled) in the same manner as that of Example 2. After the content was cooled, it was centrifuged. As a result, sedimentation of a black solid was observed. The analyses of metals for the solutions before and after the distillation revealed that 25%, based on the amount of the rhodium contained in the solution before distillation, of rhodium was sedimented during distillation, etc.

Comparative Example 4

90 g of the same concentrated catalyst solution as that used for subjecting the carbonylation treatment in Example 5 was heat-treated (distilled) in the same manner as that of Example 2. After the content was cooled, it was centrifuged. As a result, sedimentation of a black solid was observed. The analyses of metals for the solutions before and after the distillation revealed that 25%, based on the amount of the rhodium contained in the solution before distillation, of rhodium was sedimented during distillation, etc.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What I claim is:

1. In a method of stabilizing a rhodium compound contained in a catalyst solution which is contaminated with tar formed as a by-product from a carbonylation reaction to produce acetic anhydride in which methyl acetate or dimethyl ether chemically reacts with carbon monoxide in the presence of a catalyst system comprising a rhodium compound and an alkali metal iodide, the improvement comprising contacting said catalyst solution with carbon monoxide and methyl iodide in an amount sufficient to obtain a methyl iodide concentration of 5 to 50 wt. % in said catalyst solution prior to separating the tar from the catalyst solution.

2. In a method of stabilizing a rhodium compound contained in a catalyst solution which is contaminated with tar formed as a by-product from a carbonylation reaction to produce acetic anhydride in which methyl acetate or dimethyl ether chemically reacts with carbon monoxide in the presence of a catalyst system comprising a rhodium compound and an alkali metal iodide, the improvement comprising contacting said catalyst solution with carbon monoxide in an amount sufficient to obtain a methyl iodide concentration of 5 to 50 wt. % in said catalyst solution prior to separating the tar from the catalyst solution.

3. In a method of stabilizing a rhodium compound contained in a catalyst solution which is contaminated with tar formed as a by-product from a carbonylation reaction to produce acetic anhydride in which methyl acetate or dimethyl ether chemically reacts with carbon monoxide in the presence of a catalyst system comprising a rhodium compound and an alkali metal iodide, the improvement comprising contacting said catalyst solution with carbon monoxide and methyl iodide in an amount sufficient to maintain a methyl iodide concentration of 5 to 50 wt. % in said catalyst solution prior to separating the tar from the catalyst solution.

4. In a method of stabilizing a rhodium compound contained in a catalyst solution which is contaminated with tar formed as a by-product from a carbonylation reaction to produce acetic anhydride in which methyl acetate or dimethyl ether chemically reacts with carbon monoxide in the presence of a catalyst system comprising a rhodium compound and an alkali metal iodide, the improvement comprising contacting said catalyst solution with carbon monoxide in an amount sufficient to maintain a methyl iodide concentration of 5 to 50 wt. % in said catalyst solution prior to separating the tar from the catalyst solution.

5. The method according to claim 1, wherein said catalyst solution contains a diluent of a solvent containing methyl iodide.

6. The method according to claim 2, wherein said catalyst solution contains a diluent of a solvent containing methyl iodide.

7. The method according to claim 3, wherein said catalyst solution contains a diluent of a solvent containing methyl iodide.

8. The method according to claim 4, wherein said catalyst solution contains a diluent of a solvent containing methyl iodide.

9. The method according to claim 1, wherein said catalyst system comprises rhodium iodide and lithium iodide.

10. The method according to claim 2, wherein said catalyst system comprises rhodium iodide and lithium iodide.

11. The method according to claim 3, wherein said catalyst system comprises rhodium iodide and lithium iodide.

12. The method according to claim 4, wherein said catalyst system comprises rhodium iodide and lithium iodide.

13. The method according to claim 1, wherein said catalyst system comprises rhodium iodide, an alkali metal iodide, an aluminum compound and a boron compound.

14. The method according to claim 2, wherein said catalyst system comprises rhodium iodide, an alkali metal iodide, an aluminum compound and a boron compound.

15. The method according to claim 3, wherein said catalyst system comprises rhodium iodide, an alkali metal iodide, an aluminum compound and a boron compound.

16. The method according to claim 4, wherein said catalyst system comprises rhodium iodide, an alkali metal iodide, an aluminum compound and a boron compound.

17. The method according to claim 1, wherein said catalyst solution comprises a concentrated catalyst solution provided by conducting flash vaporization after the carbonylation reaction.

18. The method according to claim 2, wherein said catalyst solution comprises a concentrated catalyst solution provided by conducting flash vaporization after the carbonylation reaction.

19. The method according to claim 3, wherein said catalyst solution comprises a concentrated catalyst solution provided by conducting flash vaporization after the carbonylation reaction.

20. The method according to claim 4, wherein said catalyst solution comprises a concentrated catalyst solution provided by conducting flash vaporization after the carbonylation reaction.

21. The method according to claim 1, wherein a step of removing a component contained in said catalyst solution having a low-boiling point is provided between the step of treating said catalyst solution and the step of separating the tar from said catalyst solution.

22. The method according to claim 2, wherein a step of removing a component contained in said catalyst solution having a low-boiling point is provided between the step of treating said catalyst solution and the step of separating the tar from said catalyst solution.

23. The method according to claim 3, wherein a step of removing a component contained in said catalyst solution having a low-boiling point is provided between the step of treating said catalyst solution and the step of separating the tar from said catalyst solution.

24. The method according to claim 4, wherein a step of removing a component contained in said catalyst solution having a low-boiling point is provided between the step of treating said catalyst solution and the step of separating the tar from said catalyst solution.

* * * * *